US009682087B2

(12) United States Patent
Sitruk-Ware et al.

(10) Patent No.: US 9,682,087 B2
(45) Date of Patent: Jun. 20, 2017

(54) NESTORONE®/ESTRADIOL TRANSDERMAL GEL

(75) Inventors: Regine Sitruk-Ware, New York, NY (US); Dario Norberto Ramon Carrara, Oberwil (CH); Arnaud Grenier, Steinbrunn le Haut (FR)

(73) Assignees: The Population Council, Inc., New York, NY (US); Antares Pharma IPL AG (CH)

( * ) Notice: Subject to any disclaimer, the term of this patent is extended or adjusted under 35 U.S.C. 154(b) by 0 days.

(21) Appl. No.: 13/515,552

(22) PCT Filed: Dec. 17, 2010

(86) PCT No.: PCT/US2010/060941
§ 371 (c)(1),
(2), (4) Date: Oct. 26, 2012

(87) PCT Pub. No.: WO2011/084668
PCT Pub. Date: Jul. 14, 2011

(65) Prior Publication Data
US 2013/0045953 A1 Feb. 21, 2013

Related U.S. Application Data
(60) Provisional application No. 61/287,514, filed on Dec. 17, 2009.

(51) Int. Cl.
*A61K 31/57* (2006.01)
*A61P 15/18* (2006.01)
*A61K 31/565* (2006.01)
*A61K 9/00* (2006.01)

(52) U.S. Cl.
CPC .......... *A61K 31/565* (2013.01); *A61K 9/0014* (2013.01); *A61K 31/57* (2013.01)

(58) Field of Classification Search
USPC ....................................................... 514/170
See application file for complete search history.

(56) References Cited

U.S. PATENT DOCUMENTS

| 5,198,223 A | 3/1993 | Gale et al. |
| 7,470,433 B2 | 12/2008 | Carrara et al. |
| 2007/0166361 A1 | 7/2007 | Carrara et al. |

FOREIGN PATENT DOCUMENTS

| JP | 06-502429 T | 3/1994 |
| JP | 07-502253 A | 3/1995 |
| JP | 04-342531 A | 10/2009 |
| WO | 91/18570 A1 | 12/1991 |
| WO | 9207589 A1 | 5/1992 |
| WO | 2011049948 A2 | 4/2011 |

OTHER PUBLICATIONS

Jarvinen (Effect of dose on the adsorption of estradiol from a transdermal gel, Maturitas 35 (2000) pp. 51-56).*
Antares Pharma and Population Council Announce Preliminary Positive Phase 2 Trial Results. May 15, 2009 <http://www.antarespharma.com/investor_relations/press/release/120/>.
Antares Pharma Inc: "Antares Pharma and Population Council Announce Preliminary Positive Phase 2 Trial Results", Clinical Trials Week via newsrx.com, Jun. 1, 2009 (Jun. 1, 2009). p. 2PP, XP009145896.
De Lignieres et al., "Biological Effects of Estradiol-17β in Postmenopausal Women: Oral Versus Percutaneous Administration", Journal of Clinical Endocrinology and Metabolism, vol. 62, No. 3, Mar. 1986.
Fraser et al., "An initial pharmacokinetic study with a Metered Dose Transdermal System for delivery of the progestogen Nestorone as a possible future contraceptive", Contraception 76 (2007) 432-438.
International Search Report and Written Opinion, PCT/US2010/060941, Dated Mar. 24, 2011.
Kemmeren et al., "Effect of second and third generation oral contraceptives on lipid metabolism in the absence or presence of the factor V Leiden mutation", Journal of Internal Medicine 2001: 250: 441-448.
Kemmeren et al., "Third generation oral contraceptives nd risk of venous thrombosis: meta-analysis", BMJ vol. 323, Jul. 21, 2001.
Kluft et al., "A prospective study on the effects on hemostasis on two oral contraceptives containing drospirenone in combination with either 30 or 20 ug ethinyl estradiol and a reference containing desogestrel and 30 ug ethinyl estradiol", Contraception 73, 336-343 (2006).
Kumar et al., "Nestorone: a progestin with a unique pharmacological profile", Steroids 65 (2000) 629-636.
Merkatz et al., "A dose-finding, cross-over study to evaluate the effect of a transdermal Nestorone(R)-Estradiol (NES/E2) gel on ovulation suppression and assess acceptability in healthy ovulating women", Fertility and Sterility, Elsevier Science Inc, New York, NY, USA, vol. 94, No. 4, Sep. 1, 2010 (Sep. 1, 2010), p. S4, XP027249960.
Press Release from Antares Pharma and Population Council Announce Phase I Results, "First Transdernmal Contraceptive Gel Contains Nestorone(R)" Nov. 28, 2007.

(Continued)

*Primary Examiner* — Kathrien Cruz
(74) *Attorney, Agent, or Firm* — Lerner, David, Littenberg, Krumholz & Mentlik, LLP

(57) ABSTRACT

The invention discloses compositions and methods for ensuring in both women of fertile age where it ensures also a contraception with additional health benefits and in post-menopausal women where it offers a hormonal therapy with additional medical benefits such as the potential for lower risk of thrombosis. The aforementioned compositions comprising NES as a potent progestational and antiovulatory agent with no androgenic nor estrogenic nor glucocorticoid effect, and combined with estradiol formulated for non-oral transdermal administration as specific daily doses.

6 Claims, 7 Drawing Sheets

(56) References Cited

OTHER PUBLICATIONS

Rad et al., "Comparative effects of a contraceptive vaginal ring delivering a nonandrogenic progestin and continous ethinyl estradiol and a combined oral contraceptive containing levonorgestrel on hemostasis variables" American Journal of Obstetrics and Gynecology (2006) 195, 72-77.
Scarabin et al., Defferential association of oral and transdermal oestrogen-replacement therapy with venous thromboembolism risk The Lancet, vol. 362: 428-32, Aug. 9, 2003.
Sitruk-Ware et al., "Nestorone: clinical application for contraception and HRT", Steroids 68 (2003) 907-913.
Sitruk-Ware, Regine, "New progestagens for contraceptive use", Human Reproduction Update, vol. 12, No. 2, pp. 169-178, 2006.
The European Agency for the Evaluation of Medicinal Products Post-authorisation Evaluation of Medicines for Huma Use, "EMEA Committee for Proprietary Medicinal Products (CPMP), CPMP Public Assessment Report", Doc. Ref: EMEA/CPMP/2201/01/en/Final, London, Sep. 28, 2001.
The Oral Contraceptive and Hermostasis Study Group, "The effects of seven monophasic oral contraceptive regimens on hemostatic variables: conclusions from a large randomized multicenter study", Contraception 67,173-185, Mar. 2003.
Vehkavaara et al., "Effects of oral and transdermal estrogen replacement therapy on markers of coagulation, fibrinolysis, inflammation and serum lipids and lipoproteins in postmenopausal women", Thromb Haemost 2001; 85: 619-625.
European Office Action for Application No. 10799204.2 dated Sep. 17, 2013.
Australian Examination Report for Application No. 2010339867 dated Jan. 30, 2014.
Canadian Office Action for Application No. 2,782,075 dated Feb. 5, 2014.
Fertility and Sterility, Sep. 2010, 94 (4, Supplement), S4.
Japanese Office Action for Application No. 2012-544866 dated Nov. 6, 2014.
Osborne et al., "Skin permeation enhancers cited in the Technical Literature", published in Pharmaceutial Technology in Nov. 1997.
Japanese Office Action for Application No. 2012-544866 dated Dec. 3, 2015.

* cited by examiner

NESTORONE®/ESTRADIOL TRANSDERMAL GEL

CROSS-REFERENCE TO RELATED APPLICATIONS

This application is a national phase entry under 35 U.S.C. §371 of International Application No. PCT/US2010/060941 filed Dec. 17, 2010, published in English, which claims the benefit of the filing date of U.S. Provisional Patent Application No. 61/287,514 filed Dec. 17, 2009, the disclosures of which are hereby incorporated herein by reference.

FIELD OF THE INVENTION

The present invention relates to the use of specific combinations of progestins and estrogens in a transdermal or transmucosal composition for use in a method of contraception for women in their reproductive years.

BACKGROUND OF THE INVENTION

Progestins are synthetic progestogens most frequently used for hormonal contraception (either alone or with an estrogen), as well as to prevent endometrial hyperplasia from unopposed estrogen in hormone replacement therapy. Estrogens, and especially the natural estrogen 17β estradiol (E2) on the other hand, are steroid compounds primarily functioning as female sex hormones and also used in certain oral contraceptives and in estrogen replacement therapy for post-menopausal women, as well as in hormone replacement therapy in various endocrinological conditions.

16-methylene-17α-acetoxy-19-norpregn-4-ene-3,20-dione is a progestin (also identified by the trade name NESTORONE® and referred to throughout this application as NES) comprising a 19-nor-progesterone derivative, with a structure close to the physiological hormone progesterone, which has been studied extensively in non-oral forms, including implants and vaginal rings for contraception. It has strong antiovulatory and progestational properties, and does not carry androgenic, estrogenic or glucocorticoid actions at therapeutic levels (1). Given its high anti-ovulatory potency when given systemically, only very low doses of NES are believed to be required for contraceptive efficacy and hence can be used in various non-oral delivery systems (2).

Estradiol (E2) is less potent than Ethinyl estradiol on the stimulation of estrogen-dependent liver proteins such as clotting factors, and has the potential to be a safer estrogen when combined with progestins for contraception. In addition it has been shown that estradiol when administered transdermally induces less risk of thrombotic events than oral estradiol when given to postmenopausal women (3).

It has been suggested that NES should be administered transdermally, either alone or in combination with estrogens such as estradiol. In particular, in a press release dated Nov. 28, 2007, Antares Pharma and The Population Council announced the results of a Phase 1 study for a contraceptive gel containing Nestorone® and estradiol. The purpose of the trial was to determine the absorption of Nestorone® and estradiol using the Antares transdermal gel system. The press release indicates that the data showed that an effective combined dose was identified for consistently delivering Nestorone®, and the serum levels matched target ranges expected to provide effective contraception. No serious adverse events were said to be recorded, and most subjects did not experience skin irritation.

As for the Antares gel system itself, this is disclosed, for example, in U.S. Pat. No. 7,470,433, the disclosure of which is incorporated herein by reference thereto.

SUMMARY OF THE INVENTION

In accordance with the present invention, a novel contraceptive has been discovered comprising a transdermal system for contraceptive treatment of females comprising a carrier formulation including an amount of a progestin comprising 16-methylene-17α-acetoxy-19-norpregn-4-ene-3,20-dione sufficient to provide absorption of a daily dose of at least about 300 µg of the progestin to the female and estradiol sufficient to provide absorption of a daily dose of at least about 100 µg of estradiol to the female, whereby the transdermal system effectively blocks ovulation in the female and follicular development and rupture are prevented while irregular bleeding is minimized. Preferably the transdermal system includes at least 3 mg of the 16-methylene-17α-acetoxy-19-norpregn-4-ene-3,20-dione and at least 1 mg of the estradiol, preferably from about 3 to 4.5 mg of the progestin and from about 1 to 1.5 mg of the estradiol. These levels of these hormones applied onto the skin result in 10% absorption, and thus correspond to a daily dose of about 300 to 450 µg of the progestin and about 100 to 150 µg of the estrogen. Expressed in a different manner, it would also be possible to equate these levels of absorption of these hormones to corresponding plasma levels in the patient. In this regard, the amounts of these hormones required for the transdermal or transmucosal devices of this invention will generally result in plasma levels for the progestin (NES) of at least about 250 pmol/L and plasma levels for the estrogen (estradiol) of at least about 300 pmol/L (100 p/ml).

In one embodiment of the transdermal system of the present invention, the carrier comprises a gel. Preferably, the gel provides a hydroalcoholic formulation including at least one penetration enhancer for the active agents in the gel system.

In accordance with another embodiment of the present invention, a method for contraceptive treatment of females is described comprising providing daily dosage units of a progestin comprising 16-methylene-17α-acetoxy-19-norpregn-4-ene-3,20-dione and estradiol in the form of a carrier formulation including an amount of a progestin comprising 16-methylene-17α-acetoxy-19-norpregn-4-ene-3,20-dione and estradiol in the form of a carrier formulation including an amount of the progestin sufficient to provide absorption of a daily dose of at least about 300 µg of the progestin to the female and an amount of the estradiol sufficient to provide absorption of a daily dose of at least about 100 µg of the estradiol to the female. In one embodiment, the method comprises providing the daily dosage units to the female sequentially on a once-daily basis for a period of three weeks followed by one week of no such daily dosage units. In accordance with another embodiment, the method comprises providing the daily dosage units to the female continuously on a daily basis.

In accordance with another embodiment of the method of the present invention, the method includes providing at least about 3 mg, and preferably from about 3 to 4.5 mg, of the 16-methylene-17α-acetoxy-19-norpregn-4-ene-3,20-dione and at least about 1 mg, and preferably from about 1 to 1.5 mg of the estradiol.

In accordance with another embodiment of the method of the present invention, the contraceptive treatment comprises a transdermal contraceptive treatment. Preferably, the daily dosage units are in the form of transdermal gel.

In accordance with the present invention, a specific combination of NES and estradiol in the form of a transdermal gel formulation has been discovered. Throughout this specification use of the term NES is intended to refer to 16-methylene-17α-acetoxy-19-norpregn-4-ene-3,20-dione, but is also intended to include derivatives of this compound which would have similar or greater potency. These can include, for example, 13-ethyl-Nestorone and other such derivatives. The specification also is directed to the use of estradiol. This natural hormone is important for use because of its high safety factor but it is appreciated that estrogens with a similar structure to estradiol may be useful in connection with this invention, although this certainly does not include ethinyl estradiol as discussed herein. Estradiol itself, however, is highly preferred in connection with this invention particularly because of the safety it exhibits in terms of venous thrombosis and the like.

In accordance with one embodiment of the present invention, a transdermal system for contraceptive treatment of females is provided comprising a carrier formulation including the progestin NES in an amount sufficient to provide absorption of a daily dose of at least 300 μg of the NES, and preferably from about 300 to 450 μg of NES to the female, as well as an amount of estradiol sufficient to provide absorption of a daily dose of at least about 100 μg of the estradiol, and preferably from about 100 to 150 μg of the estradiol, to the female. In the case of a transdermal system, it has been found that these amounts of the progestin and the estradiol can be provided to the patient for such a system comprising a carrier formulation including at least 3 mg of NES, and preferably from 3 to 4.5 mg of NES, and at least 1 mg of estradiol, and preferably from 1 to 1.5 mg of estradiol, whereby the transdermal system effectively blocks ovulation in the female, and follicular development and rupture are prevented while irregular bleeding is minimized. In a preferred embodiment, the carrier comprises a gel, and in particular a hydroalcoholic gel, and including at least one penetration enhancer for the active agents in the system.

In accordance with this invention, NES has thus been effectively administered transdermally in a gel formulation in which it is rapidly absorbed through the skin, resulting in absorption in amounts sufficient to block ovulation and to achieve the other important results of the present invention, without many of the potential side effects of the prior art.

The available hormonal methods are based on synthetic contraceptive steroids, and generally include Ethinyl estradiol (EE), which is a potent synthetic estrogen. These combinations, whether delivered orally or by means of transdermal route, induce metabolic changes related to a stimulatory action on the synthesis of liver proteins, such as low and high-density lipoproteins and clotting factors. The latter changes have been suggested as one mechanism possibly associated with the increased risk in venous thromboembolism (VTE) in oral contraceptive users (4,5). With new progestins, either from the third generation (such as norgestimate or etonogestrel) which are less androgenic than those of the second generation (such as levonorgestrel) or the more recent progestins (such as drospirenone, trimegestone or NES) which are not at all androgenic (6), the impact of Ethinyl estradiol on the liver is not "opposed" as with the more androgenic progestins. Therefore, higher levels of sex hormone-binding globulin (SHBG) and high-density lipoprotein (HDL) were found when third generation oral contraceptives were used, but were considered to be a beneficial aspect as far as HDL changes were concerned (7). However, changes also occur with the clotting factors that are estrogen-dependent, and the variation of some coagulation factors is higher with these combinations than with the second generation oral contraceptives. Although there is no true surrogate marker of VTE risk identified so far, the difference observed in the incidence of VTE in users of third generation rather than second generation oral contraceptives suggested a higher and uncontrolled impact of EE on the regulation of hemostasis (8-11).

In studies conducted with steroids closer to the physiological hormones progesterone and estradiol, it has been shown that the risk of VTE is lower in users of transdermal estradiol as compared with oral estradiol (3). Transdermal estradiol is a much less potent estrogen that EE, and its impact on the liver proteins and coagulation factors is almost nil. (12).

Therefore, the use of powerful progestins such as NES, which has a neutral metabolic profile, and estradiol, rather than Ethinyl estradiol, in a transdermal formulation is extremely attractive because (1) it improves the safety profile of these contraceptives; and (2) it delivers contraceptive hormones which are close to the physiological hormones 17β-estradiol and progesterone.

The concept underlying the present invention is to base the contraceptive effect of the combination on the progestin only, and to use the small dose of estradiol as an add-back therapy. NES is a very powerful antiovulatory agent, and has proved to block ovulation in more than 95% of the subjects when used at doses leading to serum levels of 250 pmol/L. With these levels, the follicular maturation is suppressed, but not completely, and only a small dose of E2 will be needed as an add-back treatment to prevent signs of hypoestrogenism and to control the bleeding pattern.

Preliminary findings from a Phase II, dose finding, crossover study to evaluate the effect of NES/E2 transdermal gel delivery in three different doses: high (4.5 mg NES/1.5 mg E2), medium (3.0 mg NES/1.0 mg E2) and low (1.5 mg NES/0.5 mg E2) showed that, while all the three doses suppressed ovulation, it was only the doses utilizing at least 3.0 mg of NES and at least 1.0 mg of E2 which not only adequately suppressed ovulation, but which also prevented follicular growth in a high proportion of subjects. Therefore, the endogenous levels of E2 were low and the addition of the 1 mg dose of exogenous E2 was sufficient as an "add-back" therapy. Indeed, this particular dosage level was particularly useful due to the stable E2 levels which reached the targeted range of the early follicular phase in women of fertile age. Although the medium and high doses of the gel formulation were both able to suppress most follicles to grow beyond 10 to 15 mm, a size of follicle observed during the early stages of their development, the addition of the exogenous dose of 1 mg of E2 allowed the serum levels to reach mid-follicular phase range (about 130 pg/ml) while the high dose gave raise to much higher levels of estrogen (about 180 pg/ml). In addition, the variations in serum levels were higher with the high dose of E2, while the medium dose gave stable delivery rates. This stable delivery of the steroids is in contrast with the peaks and troughs usually observed with oral administration of the same estrogen.

In accordance with a preferred embodiment of the present invention, these particularly advantageous doses of NES and E2 are applied transdermally in the form of a hydroalcoholic gel, preferably along with at least one permeation enhancer, and most particularly along with a specific combination of permeation enhancers. This system offers the advantage of being easy to apply and invisible cosmetically, which is expected to provide considerable appeal to women. Furthermore, this invention includes the simultaneous delivery of more than one active agent from the same gel formulation.

In this case, estradiol (E2), the naturally occurring form of estrogen, is applied along with the NES. This combination of NES and E2, which are close to the female physiological hormones, and are not administered orally, would be safer than most hormonal contraceptives which contain Ethinyl estradiol (EE), the widely used potent synthetic form of estrogen. Simultaneously, E2 will prevent hypoestrogenic symptoms. With the appropriate dosing of this invention, E2 thus also minimizes irregular bleeding that sometimes occurs when women use progestin-only contraceptives, and which can be a major source of dissatisfaction/discontinuation.

BRIEF DESCRIPTION OF THE DRAWINGS

The nature and details of the present invention may be more fully appreciated with reference to the following Detailed Description, which in turn refers to the Figures, as follows.

DETAILED DESCRIPTION

Figure 1:
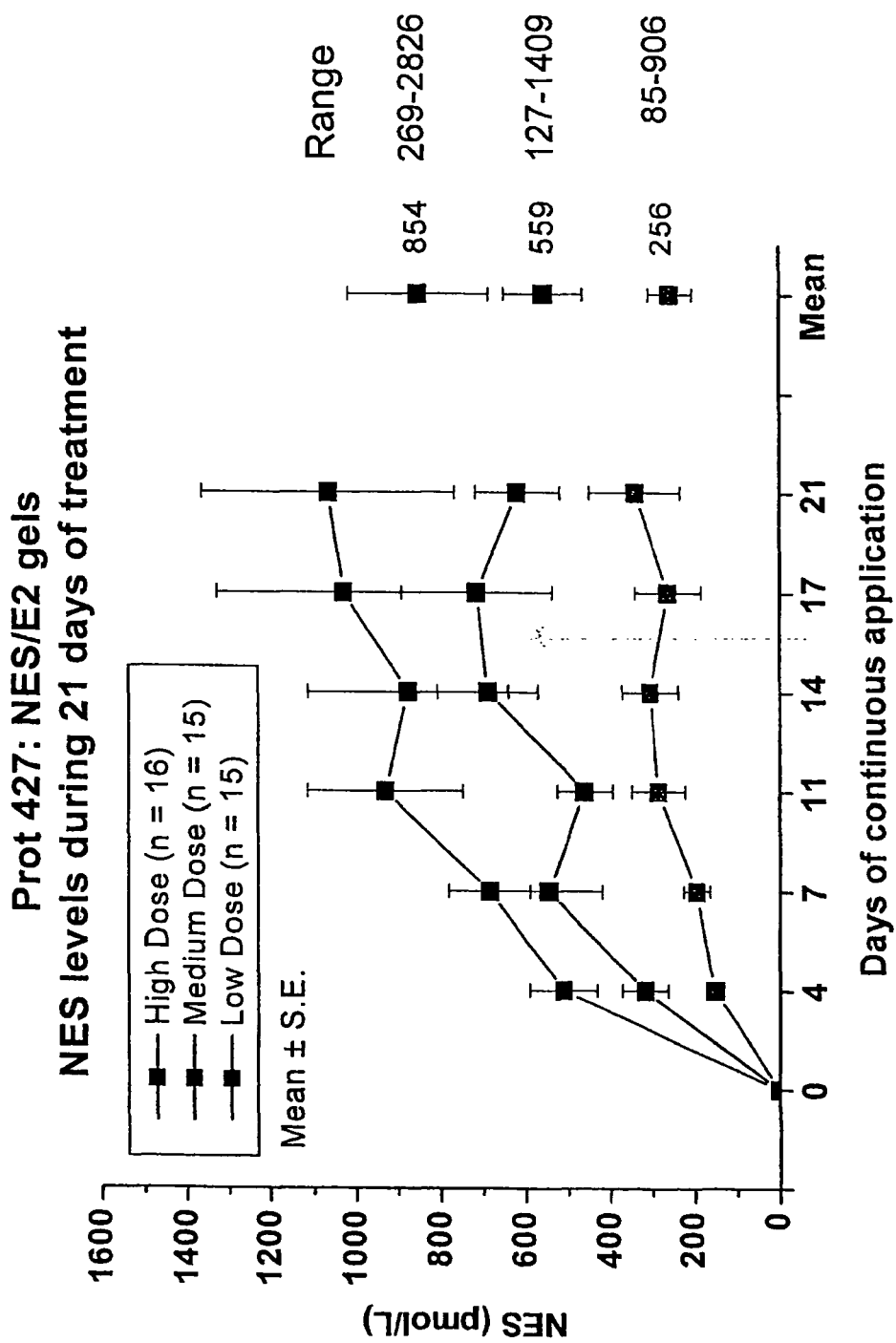
FIG. 1 is a graphical representation of the dose response for NES at various dosage levels over 21 days of use.

The first essential component of the contraceptive formulation of the present invention is the progestin NES. NES itself is a 19-nor-progesterone derivative which exerts a potent progestational and anti-ovulatory action and which does not carry androgenic or estrogenic or glucocorticoid actions at therapeutic levels. NES is 16-methylene-17α-acetoxy-19-norpregn-4-ene-3,20-dione, and is a known potent progestin when given parenterally. NES, however, is not active when administered orally.

The other critical component of the compositions of the present invention is estradiol. Estradiol itself (or 17β-estradiol) is a female sex hormone and represents the major estrogen in humans. It is used for treatment of the symptoms of menopause or as a replacement of estrogen deficiency.

The use of the term "transdermal" in accordance with this invention is meant to apply to means for application of active agents and other drug compositions through the skin, including by means of gels, creams, lotions, sprays, patches, and the like. In each case, however, the transdermal composition itself must include sufficient NES to provide absorption of a daily dose of at least about 300 μg of NES to the user, and absorption of a daily dose of at least about 100 μg of estradiol to the user, and most particularly the ratio of the absorption levels with regard to the amount of NES to the amount of estradiol should be about 3:1 in each instance. While the specification has emphasized the specific use of a gel formulation for the transdermal systems of the present invention, those of ordinary skill in this art will appreciate the fact that the formulation of this invention may also be in the form of a spray, ointment, aerosol, suppository, vaginal dosage form, as well as a patch, buccal and sublingual tablets, or other passive or active transdermal devices for absorption through the skin or mucosal surface. In each of these cases, as has been shown herein the application of the required amounts of NES and estradiol in the ratios and amounts sufficient to produce absorption of a daily dose of at least about 300 μg of the progestin and at least about 100 μg of the estradiol are the critical factors in connection with this invention. Those of ordinary skill will thus be able to readily produce a corresponding spray, ointment, aerosol or the like employing conventional systems with the specific active ingredients of the present invention therein. The present invention is also applicable to transmucosal systems, in which the carrier composition containing the NES and estradiol components is applied to the mucosa (either vaginal or buccal), in this case in order to obtain the desired plasma levels of at least about 250 pmol/L of NES and at least bout 300 pmol/L (100 p/ml) of estradiol, a different amount of these ingredients in an appropriate carrier would be required. It is thus realized that for transmucosal application a carrier which is alcohol based would not be well tolerated by the mucosa. Furthermore, far lower amounts of these hormones would be required where the mucosa exhibits far greater absorption. Thus only about 200 to 300 μg of NES would be required to obtain the necessary absorption, and only about 80 to 100 μg of estradiol will be required. These amounts can be determined by one of ordinary skill in this art in order to provide the required absorption and plasma levels of this invention.

As used herein, the term "DDU" refers to a "daily dosage unit" in which the daily dosage unit itself is contained in a transdermal formulation.

As used herein, the term "contraceptive agent" refers to medications administered in order to prevent or reduce the likelihood of pregnancy.

The transdermal systems of the present invention for the supply of a contraceptive agent specifically comprise a carrier formulation, preferably in the form of a gel, which includes at least 3 mg of NES and at least 1 mg of estradiol. In this manner, it has been found that this transdermal system can exert anti-ovulating efficacy as well as full follicular suppression, again when applied in a transdermal manner, and the inclusion of estradiol provides an "add-back" estrogen therapy which exactly matches the mid-follicular levels of estradiol in the normal cycle of untreated fertile women with a stable delivery rate. Thus, this transdermal system both suppresses ovulation and replaces the endogenous levels of estrogen at the ideal mid-follicular phase range.

At the DDU levels of this invention, the application of at least 3 mg of NES, preferably between 3 and 4.5 mg of NES, in a transdermal manner, and an absorption rate of approximately 10%, results in about 300 to 450 μg/day of NES, while the use of at least 1 mg of estradiol, and preferably from 1 to 1.5 mg of estradiol, at the same absorption rate results in about 100 to 150 μg/day of estradiol.

The transdermal application of this composition with the combination of NES and estradiol is, as noted above, preferably applied in the form of a gel. In particular, these gels may be clear, water-washable, cool to the touch, quick drying, spreadable, and/or non-greasy formulations. In particular, the components of the gel primarily include a polyalcohol, a $C_2$ to $C_4$ alkanol, and at least one permeation enhancer. The polyalcohol is preferably propylene glycol, dipropylene glycol, or mixtures thereof. The polyalcohol is preferably present in amounts of from 1 to 30 wt. % of the overall vehicle, preferably from 10 to 20 wt. % thereof. The $C_2$ to $C_4$ alkanol preferably is a $C_2$ to $C_4$ alcohol such as ethanol, isopropanol, n-propanol, or mixtures thereof, and is preferably present in amounts of from about 5 to 85 wt. %, preferably from about 30 to 60 wt. %. The permeation enhancer includes a monoalkyl ether of diethylene glycol, for the purpose of enhancing the permeation of the active agent through dermal or mucosal surfaces. This component is preferably present in the overall composition in amounts of from about 1 to 15 wt. %, preferably between about 2.5 to 7.5 wt. %.

The formulations of the present invention can also include a further permeation enhancer, such as those set forth, for example by Osborne and Henke in "Skin Permeation Enhancers Cited in the Technical Literature" published in Pharmaceutical Technology in November 1997, the disclosure of which is incorporated herein by reference thereto. In particular, the formulation of the present invention further includes a fatty alcohol, for the purpose of enhancing the permeation of the active agent even more through dermal or mucosal surfaces. This component is preferably present in the overall composition in amounts of from about 0.1 to 5 wt. %, preferably between about 0.5 to 2.0 wt. %. Most preferred fatty alcohols are myristyl alcohol and 1-tetradecanol.

The formulation may further include a thickening agent or gelling agent present in an amount sufficient to alter the viscosity of the formulation. A gelling agent can be selected from the group including: carbomer, carboxyethylene or polyacrylic acid such as Carbopol 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, Methocel grades; natural gums such as arabic, xanthan, guar gums, alginates; polyvinylpyrrolidone derivatives such as Kollidon grades; polyoxyethylene polyoxypropylene copolymers such as Lutrol F grades 68, 127. Other gelling agents include chitosan, polyvinyl alcohols, pectins, veegum grades. A tertiary amine, such as triethanolamine or trolamine, can be included to thicken and neutralize the system.

A polymer or copolymer of acrylic acid, such as a carbomer acts as a gelling forming and facilitates the release of lipophilic active agent and penetration enhancer. Preferably, the gelling agent is Lutrol F grades and Carbopol grades. The gelling agent is present from about 0.2 to about 30.0% w/w of the formulation depending on the type of polymer. For example, the gelling agent is preferably present in an amount between about 0.5% to 2% for polyacrylic acids, and between about 1 to 5% for celluloses.

The amount and the type of the gelling agent in the formulation may be selected to provide the desired product consistency and/or viscosity to facilitate application to the skin.

The formulation may further include preservatives such as, but not limited to, benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10.0% w/w depending on the type of compound.

The formulation may optionally include antioxidants such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant is present from about 0.001 to about 5.0% w/w of the formulation depending on the type of compound.

The formulation may further include buffers such as carbonate buffers, citrate buffers, phosphate buffers, acetate buffers, hydrochloric acid, lactic acid, tartric acid, diethylamine, triethylamine, diisopropylamine, aminomethylamine. Although other buffers as known in the art may be included. The buffer may replace up to 100% of the water amount within the formulation.

The formulation may further include humectant, such as but not limited to glycerin, propylene, glycol, sorbitol, triacetin. The humectant is present from about 1 to 10.0% w/w of the formulation depending on the type of compound.

The formulation may further include a sequestering agent such as edetic acid. The sequestering agent is present from about 0.001 to about 5.0% w/w of the formulation depending on the type of compound.

The formulation may further include anionic, non-ionic or cationic surfactants. The surfactant is present from about 0.1% to about 30.0% w/w of the formulation depending on the type of compound.

Optionally, the formulation may include a pH regulator, generally a neutralizing agent, which can optionally have crosslinking function. By way of example and not limitation, the pH regulator may include a ternary amine such as triethanolamine, tromethamine, tetrahydroxypropylethylendiamine, NaOH solution. The pH regulator is present in the formulations in about 0.05 to about 2.0% w/w.

Optionally, the formulation may include moisturizers and/or emollients to soften and smooth the skin or to hold and retain moisture. By way of example and not limitation, moisturizers and emollients may include cholesterol, lecithin, light mineral oil, petrolatum, and urea.

The overall nature of the gel formulations of the present invention includes those set forth, for example, in U.S. Pat. No. 7,470,433, the disclosure of which is incorporated herein by reference thereto.

As noted above, however, other formulations appropriate for the transdermal delivery of the two steroids NES and E2 described herein are possible. This transdermal delivery can be carried out by means of a transdermal patch, or by means of a transdermal spray, or Metered Dose Transdermal System (MTDS). It has been shown with the latter that levels of 250 pmol/L of NES could be reached with two applications of the spray onto the skin (13). The addition of an appropriate dose of E2 to the achieved dose of NES would be another form of transdermal delivery for contraceptive purpose with the above-discussed additional benefits in terms of safety. Transdermal matrix patches delivering both NES and E2 in a surface of around 20 to 30 cm$^2$, delivering 300 µg of NES and 100 µg of E2 daily (and in particular, delivery of the NES and the E2 at a ratio of about 3:1) can also achieve such objectives, with an additional possibility of delivering it over 7 days continuously, according to the matrix design selected.

An additional finding made both with the gel formulations as well as with the MDTS formulations, was to still observe detectable levels of NES after up to 72 hours, a much longer half-life than that observed with any other route of administration of the steroid. This finding is explained by a retention of the steroid into the stratum corneum, the upper layer of the skin, which then constitutes a reservoir from which the progestin is released. The additional details for transdermal spray and MDTS are known in the art, such as in the articles discussed herein, which are incorporated herein by reference thereto.

The transdermal contraceptives of the present invention are preferably employed either continuously, that is each day by the patient, or sequentially, that is, for example, each day for three weeks each month, followed by one week of no drug dosage application. Another regimen would be that of 24 days of gel application followed by 4 days of no gel treatment application. These formulations thus additionally offer replacement of estrogen levels at physiological levels.

Use of the transdermal compositions of the present invention comprises a method for contraceptive treatment by applying the DDU discussed above for daily administration in the manners set forth herein. The transdermal or non-oral formulations of the present invention are thus applied in the form discussed above, preferably as a gel or the like.

EXAMPLES

Figure 2:
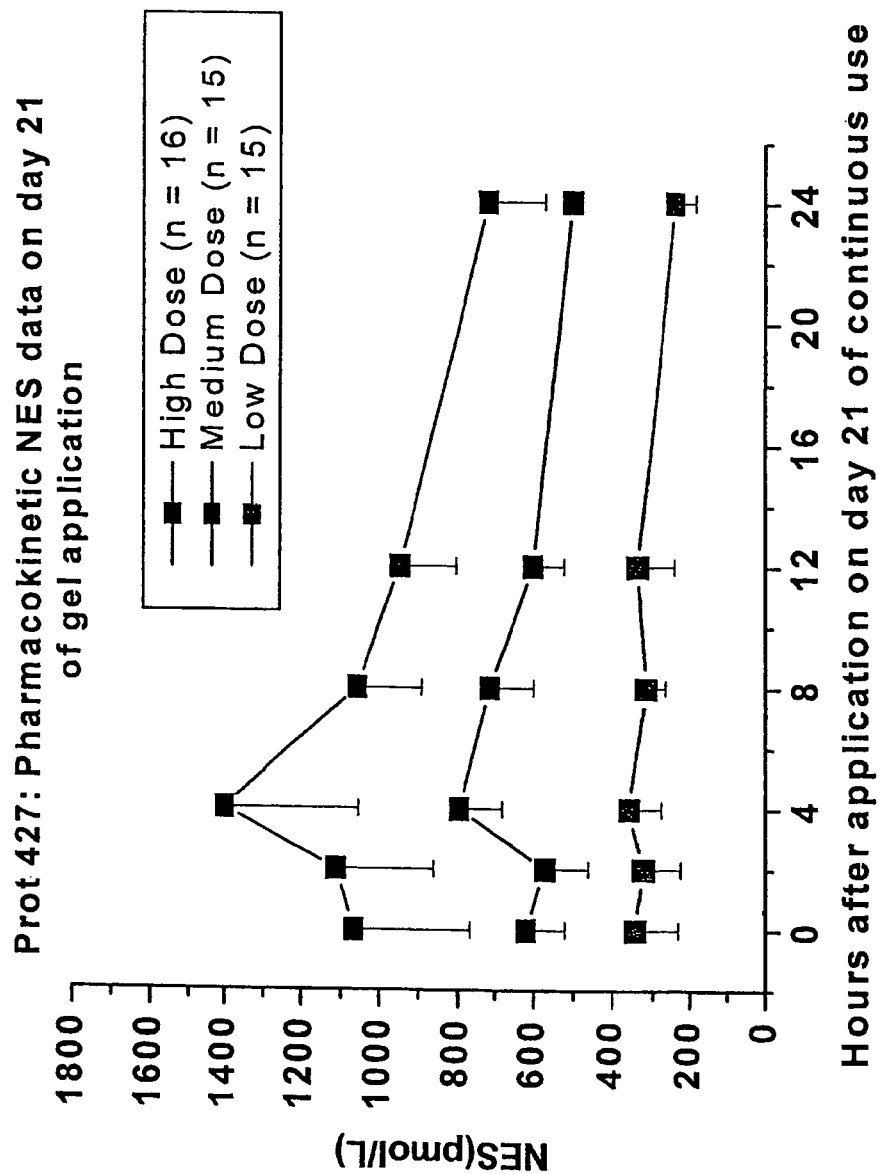
FIG. 2 is a graphical representation of the measure of serum levels for NES at various dosage levels at different time points on the last day (day 21) of the treatment cycle.

The present invention was initially exemplified by a number of women who received the three different doses (high, medium and low, as discussed above) of the transdermal combination of NES and E2 in the form of a gel, for one cycle each, separated by a wash-out cycle to resume ovulation before the next dose was tested. The mean levels of NES obtained with the 3 doses tested show a dose-response, as can be seen in FIG. 1. The lowest dose permitted the subjects to reach the mean serum levels of 250 pmol/L needed to suppress ovulation, and higher doses were attained with the medium and high doses of the gel combination. Furthermore, the serum levels of NES obtained with these three doses after a period of 24 hours can be seen in FIG. 2. Once again, the lowest dose permitted the mean serum levels of 250 pmol/L to be obtained.

Figure 3:
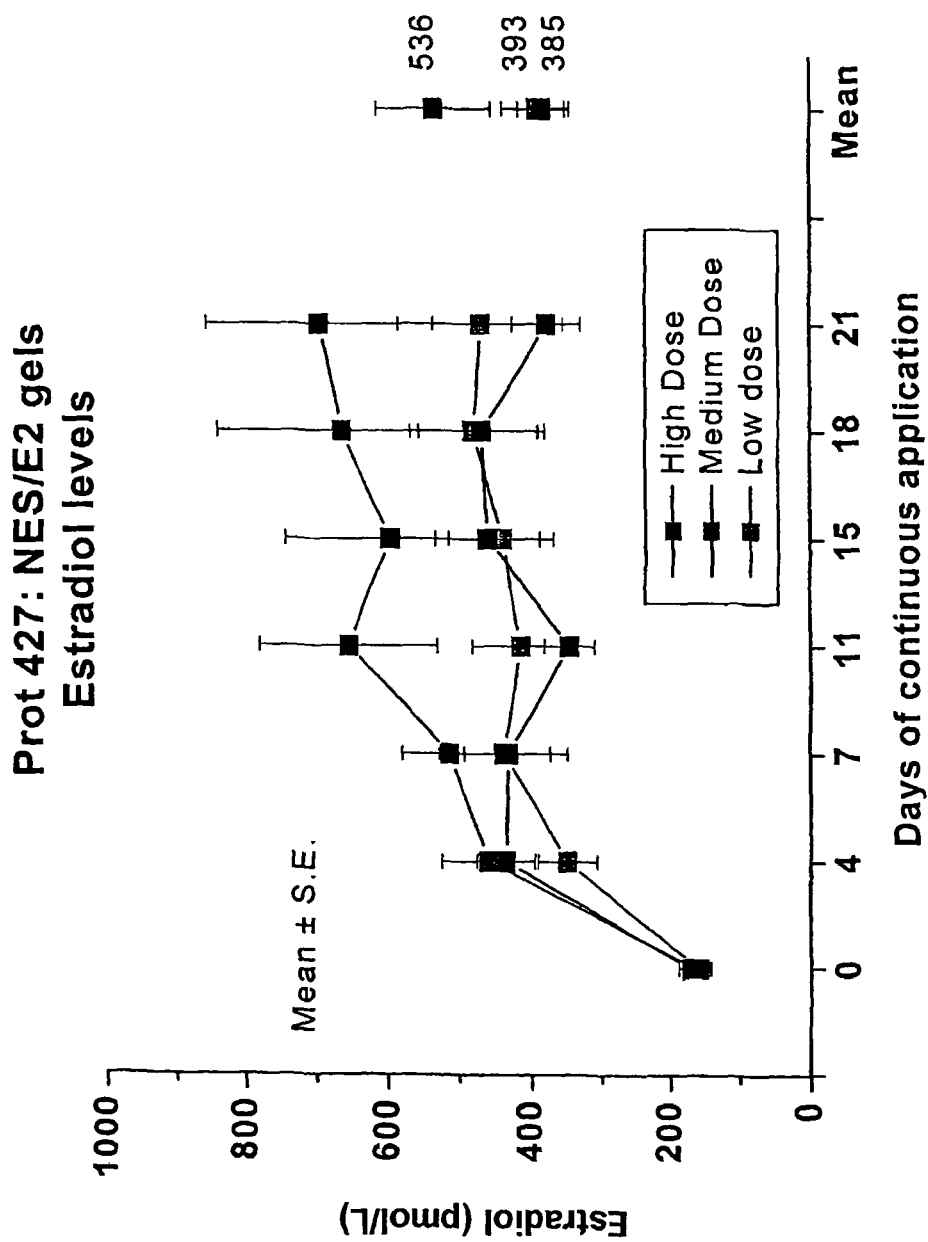
FIG. 3 is a graphical representation of estradiol levels at various dosage levels over 21 days of use.
Figure 4:
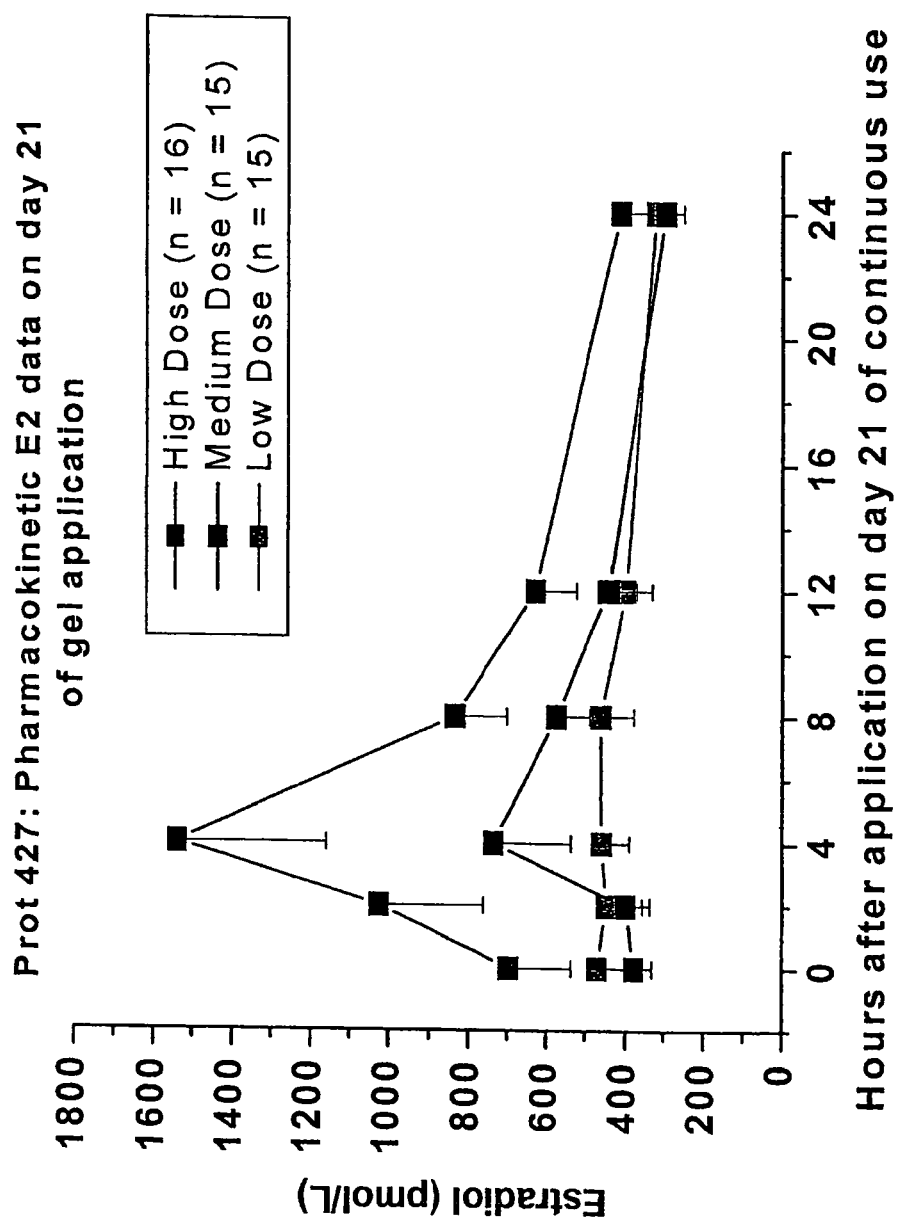
FIG. 4 is a graphical representation of the measure of serum levels for estradiol at various dosage levels at different time points on day 21 of the treatment cycle.

The estradiol levels which are measured reflected the addition of the endogenous secretion of E2 by the ovary and the exogenous dose of E2 administered in the gel itself. As seen in FIG. 3, the lowest dose of gel delivering 0.5 mg/day of E2, shows at some points a higher level than that observed with the medium dose, delivering 1 mg of E2/day. This reflects the remaining endogenous production of E2, as the follicle growth was not suppressed fully with the lower dose of NES. In addition, the serum levels of estradiol obtained with each of these dosages over a 24 hour period or on the last day of application (day 21) are shown in FIG. 4.

Figure 5:
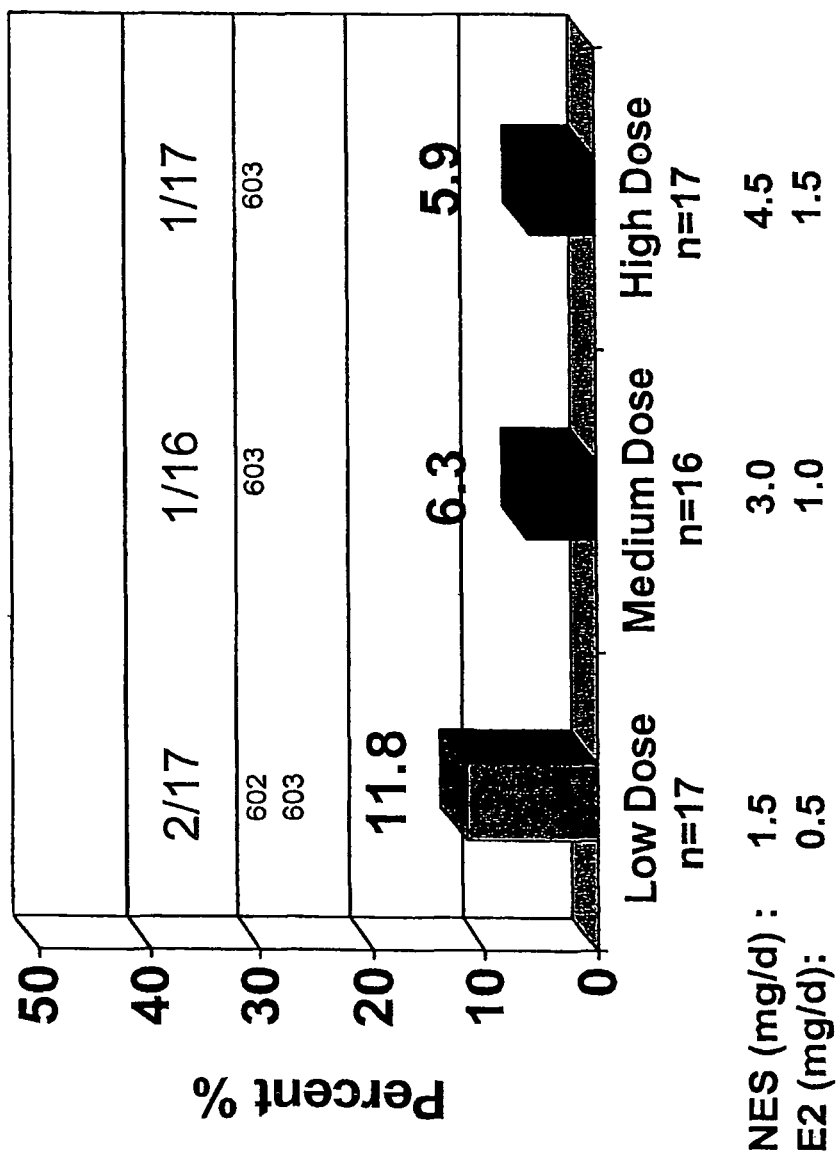
FIG. 5 is a graphical representation of the percentage of ovulatory cycles at various dosage levels.
Figure 6:
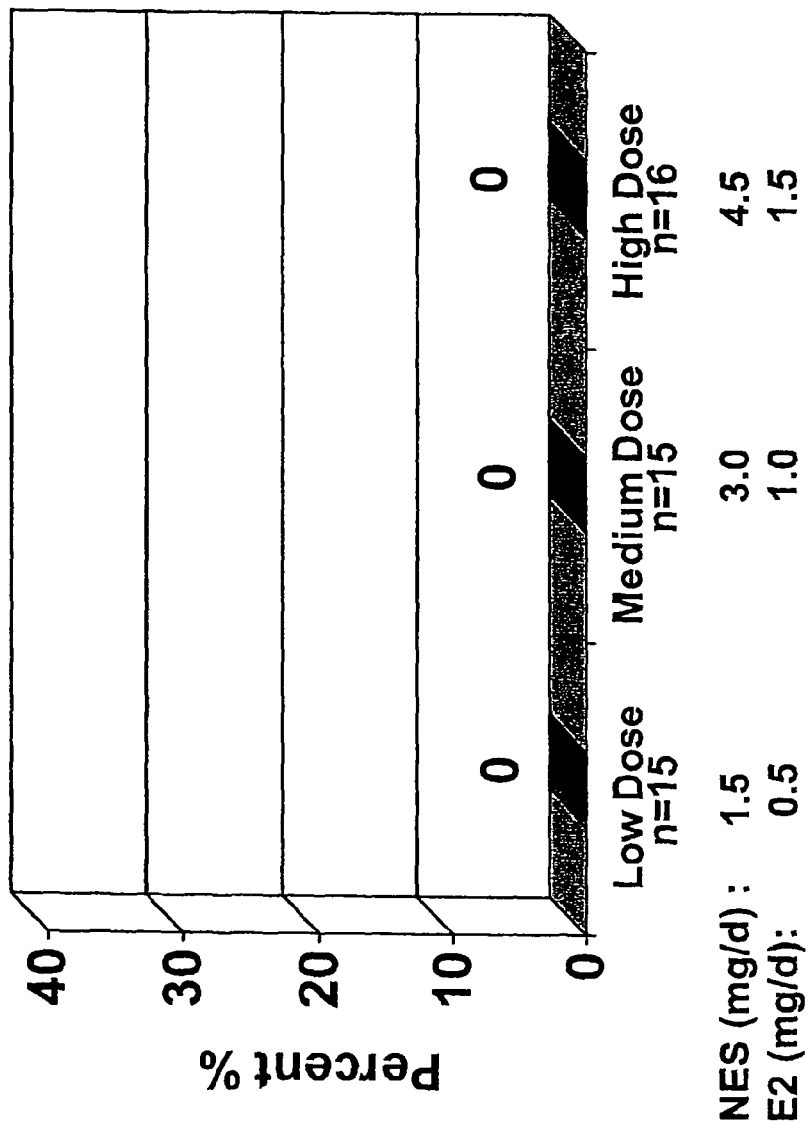
FIG. 6 is a graphical representation of the percentage of ovulating cycles at various dosage levels in compliant subjects.

The percentage of ovulary cycles in terms of follicle rupture for each of the three dosages is shown in FIG. 5. Furthermore, as shown in FIG. 6, the three different dosages tests achieved complete suppression of ovulation in women who were compliant, as assessed by measures of serum levels of NES.

Figure 7:
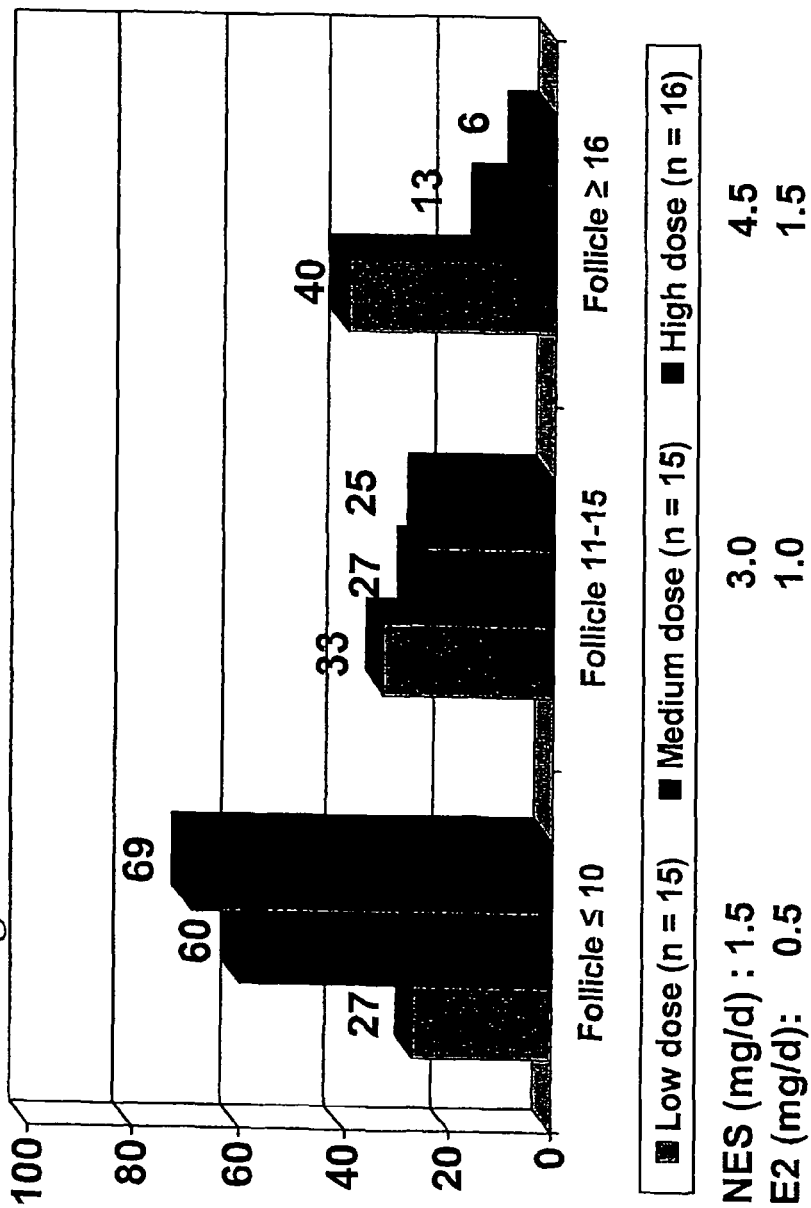
FIG. 7 is a graphical representation of follicular development at various dosage levels.

As shown in FIG. 7, the findings indicate that the lowest dose does not block the follicular growth sufficiently, as there are still 40% of the follicles which are large, at 16 mm and above, that can be triggered for ovulation in case of missed daily doses. Therefore, although the serum levels of 250 pmol/L of NES are reached and achieved ovulation suppression, this level was nevertheless not sufficient to totally prevent the growth of the follicles.

However, the medium dose has only 13% of those large follicles, showing a better control on suppression of follicle growth. While the high dose achieves the highest suppression of follicle growth, the serum levels of E2 are too high and show larger individual variations than with the medium dose of NES/E2 3 mg/1 mg daily gel application.

Indeed, with the medium dose delivering 3 mg of NES and 1 mg of E2, the mean serum levels of E2 were around 385 pmol/L (~130 pg/ml) a level found during the mid-follicular phase of a normal cycle in untreated fertile women, and sufficient to prevent hypoestrogenic symptoms and unwanted effects, such as bone loss, that may occur when E2 levels are low. (lower than 30 pg/ml). Also, the curve of E2 levels observed with the medium dose showed very stable levels of E2, with minimal variations.

All of the above demonstrates the criticality and significance of the specific use of the amounts of NES and estradiol in combination in the transdermal systems of the present invention for the contraceptive treatment of females. It has been found that only with the use of these particular levels of the active agents in question were all of the desired results of the present invention, including not only preventing ovulation in 100% of the cases, achieved therewith, but also in terms of safety, with good bleeding control, efficacy in suppressing follicle growth to a size usually seen in early follicular phase, and appropriate hormonal levels of estrogen to replace the endogenous secretion.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention provides a pharmaceutical formulation for the contraceptive treatment of females. Thus, the specific composition and drug amounts of the present invention can provide a transdermal product, preferably in the form of a gel, which can be readily and advantageously applied to the skin of a female in order to achieve extremely advantageous contraceptive effects.

REFERENCES

1. Kumar N, Koide S S, Tsong Y, Sundaram K. Nestorone: a progestin with a unique pharmacological profile. Steroids 2000; 65(10-11):629-36
2. Sitruk-Ware R, Small M, Kumar, N, Tsong Y Y, Sundaram K, Jackanicz T. Nestorone® Clinical applications for contraception and HRT. Steroids 2003, 68: 907-913.
3. Scarabin P Y, Oger E, Plu-Bureau G, et al. Differential association of oral and transdermal oestrogen-replacement therapy with venous thromboembolism risk. Lancet 2003; 362 (9382):428-432
4. Kluft C, Endrikat J, Mulder S M, Gerlinger C, Heithecker R. A prospective study on the effects on hemostasis of two oral contraceptives containing drospirenone in combination with either 30 or 20 microg Ethinyl estradiol and a reference containing desogestrel and 30 microg ethinyl estradiol. Contraception. 2006 April; 73(4):336-43.
5. Vehkavaara S, Silveira A, Hakala-Ala-Pietila T, Virkamaki A, Hovatta O, Hamsten A, Taskinen M R, Yki-Jarvinen H. Effects of oral and transdermal estrogen replacement therapy on markers of coagulation, fibrinolysis, inflammation and serum lipids and lipoproteins in postmenopausal women. Thromb Haemost. 2001 April; 85(4):619-25.

6. Sitruk-Ware R. New progestagens for contraceptive use. Hum. Reprod. Update. 2006; 12(2):169-78
7. Kemmeren J M, Algra A, Grobbee D E. Effect of second and third generation oral contraceptives on lipid metabolism in the absence or presence of the factor V Leiden mutation. J Intern Med 2001; 250:441-8
8. Kemmeren J M, Algra A, Grobbee D E. Third generation oral contraceptives and risk of venous thrombosis: meta-analysis. BMJ 2001; 323:131-4
9. EMEA Committee for Proprietary Medicinal Products (CPMP). Combined oral contraceptives and venous thromboembolism. 1-7. Sep. 28, 2001. London, UK, EMEA. CPMP Public Assessment Report
10. The effects of seven monophasic oral contraceptive regimens on hemostatic variables: conclusions from a large randomized multicenter study. Contraception 2003; 67:173-85
11. Rad M, Kluft C, Menard J, Burggraaf J, de Kam M L, Meijer P et al. Comparative effects of a contraceptive vaginal ring delivering a nonandrogenic progestin and continuous ethinyl estradiol and a combined oral contraceptive containing levonorgestrel on hemostasis variables. Am J Obstet Gynecol 2006
12. De Lignieres B, Basdevant A, Thomas G, Thalabard J C, Mercier-Bodard C, Conard J et al. Biological effects of estradiol-17 beta in postmenopausal women: oral versus percutaneous administration. J Clin Endocrinol Metab 1986; 62:536-41.
13. Fraser I S, Weisberg E, Kumar N, Kumar S, Humberstone A J, McCrossin L, Shaw D, Tsong Y Y, Sitruk-Ware R. An initial pharmacokinetic study with a Metered Dose Transdermal System for delivery of the progestogen Nestorone as a possible future contraceptive. Contraception. 2007 December; 76(6):432-8.

The invention claimed is:

1. A transdermal formulation for contraceptive treatment of females comprising a formulation in the form of a gel including an amount of a progestin comprising 16-methylene-17α-acetoxy-19-norpregn-4-ene-3,20-dione sufficient to provide absorption of a daily dose of at least about 300 μg up to about 450 μg of said progestin to said female and estradiol sufficient to provide absorption of a daily dose of at least about 100 μg up to about 150 μg of said estradiol to said female, wherein the formulation includes from 3 to 4.5 mg of said progestin and from 1 to 1.5 mg of said estradiol whereby said transdermal formulation effectively blocks ovulation in the female and follicular development and rupture are prevented while irregular bleeding is minimized.

2. The transdermal formulation of claim 1, wherein said amount of said progestin in the formulation is 3 mg and said amount of said estradiol in the formulation is 1 mg.

3. The transdermal formulation of claim 1 wherein said gel comprises a hydroalcoholic formulation including at least one penetration enhancer for the active agents in said gel system.

4. A method for transdermal contraceptive treatment of females comprising providing daily dosage units of the formulation of claim 1 to provide absorption of a daily dose of at least about 300 μg up to about 450 μg of said progestin to said female and an amount of said estradiol sufficient to provide absorption of a daily dose of at least about 100 μg up to about 150 μg of said estradiol to said female.

5. The method of claim 4 comprising providing said daily dosage units to said female sequentially on a once-daily basis for a period of 3 weeks followed by 1 week of no such daily dosage units.

6. The method of claim 4 comprising providing said daily dosage units to said female continuously on a daily basis.

* * * * *